| United States Patent [19] | [11] | 4,166,847 |
|---|---|---|
| Mitsui | [45] | Sep. 4, 1979 |

[54] ANTI-NICOTINE AGENT PREPARED FROM A SACCHARIDE AND ROSIN OR TURPENTINE

[75] Inventor: Hisashi Mitsui, Yokohama, Japan

[73] Assignee: Miya Ozawa, Yokohama, Japan

[21] Appl. No.: 773,482

[22] Filed: Mar. 2, 1977

[30] Foreign Application Priority Data

Mar. 22, 1976 [JP] Japan .................................. 51-30992

[51] Int. Cl.$^2$ ......................... A61K 31/70; C07H 3/02
[52] U.S. Cl. ....................................... 424/180; 536/1; 536/115; 536/119
[58] Field of Search .............................. 424/180; 536/1

[56] References Cited

U.S. PATENT DOCUMENTS 3,720,660  3/1973  Arendt et al. ............................ 536/1

*Primary Examiner*—Johnnie R. Brown
*Attorney, Agent, or Firm*—Stevens, Davis, Miller & Mosher

[57] ABSTRACT

An anti-nicotine agent including the combination of a monosaccharide or disaccharide, acetic acid or glacial acetic acid, rosin or turpentine, and an aqueous 28% ammonia solution.

4 Claims, No Drawings

ANTI-NICOTINE AGENT PREPARED FROM A SACCHARIDE AND ROSIN OR TURPENTINE

FIELD OF THE INVENTION

This invention relates to a new anti-nicotine agent.

BACKGROUND OF THE INVENTION

The adverse effects of nicotine on the human system which are occasioned by habitual smoking have aroused grave public concern in recent years. In spite of such circumstances, no proper anti-nicotine agent for effectively inhibiting nicotinism has been made available.

SUMMARY OF THE INVENTION

A primary object of this invention, therefore, is to provide an effective anti-nicotine agent.

This and other objects of this invention will become apparent from the following description of the invention.

As the result of a study for providing a desirable anti-nicotine agent, it has been discovered that a viscous or solid substance, which is obtained by mixing a monosaccharide or disaccharide, acetic acid or glacial acetic acid, rosin or turpentine and an aqueous 28% ammonia solution at specific ratios and heating the resultant mixture so as to rid it of water contained therein, functions advantageously as an anti-nicotine agent.

According to the present invention, there is provided an anti-nicotine agent, which is made up of a monosaccharide or disaccharide, acetic acid or glacial acetic acid, rosin or turpentine and an aqueous 28% ammonia solution in the respective amounts falling in the range of from 45:1:30:6 to 450:10:300:60 parts by weight.

DETAILED DESCRIPTION OF THE INVENTION

The agent of the present invention is made up of a monosaccharide or disaccharide, acetic acid or glacial acetic acid, rosin or turpentine and an aqueous 28% ammonia solution. Examples of the monosaccharides which are usable in this kit include dextrose and fructose. A typical example of the disaccharides which are usable is maltose. Acetic acid or glacial acetic acid indicated above as one component may be substituted by acetic anhydride. Of these forms of acetic acid, glacial acetic acid is used particularly to advantage. The rosin mentioned above is that which is obtained by removing turpentine oil from the balsam of pine trees. In the kit of the present invention, the components, namely, monosaccharide or disaccharide, acetic acid or glacial acetic acid, rosin or turpentine and an aqueous 28% ammonia solution, are required to be present in respective amounts falling in the range of from 45:1:30:6 to 450:10:300:60 parts by weight. When their amounts deviate from the aforementioned range, it is difficult to obtain the anti-nicotine agent as desired. The agent may additionally incorporate therein from 2 to 20 parts by weight of burnt alum prior to use, so that the anti-nicotine agent to be produced therefrom provides an even better anti-nicotine effect.

Now, typical examples of the formulation for the agent of this invention will be cited below.

| Formulation (1): | |
|---|---|
| Dextrose or maltose | 1,350 g |
| Glacial acetic acid | 30 ml |
| (Acetic acid) | (90 ml) |
| Rosin or turpentine | 900 g |
| Aqueous 28% ammonia solution | 180 ml |
| Formulation (2): (Formulation (1) + burnt alum) | |
| Dextrose or maltose | 1,350 g |
| Glacial acetic acid | 30 ml |
| (Acetic acid) | (90 ml) |
| Rosin or turpentine | 900 g |
| Aqueous 28% ammonia solution | 180 ml |
| Burnt alum | 60 g |

The production of an anti-nicotine agent by use of the formulation (1) or (2) above is accomplished by mixing the indicated ingredients in the corresponding amounts and heating the resultant mixture at a temperature of about 100° C. to 120° C. until it is deprived substantially completely of its water content by evaporation. Consequently, there is obtained a viscous or solid anti-nicotine agent.

The production of an anti-nicotine agent may otherwise be accomplished by the following procedure:

Firstly, 1,350 g of dextrose or maltose and 30 ml of glacial acetic acid (or 90 ml of acetic acid) are mixed and the resultant mixture is heated at a suitable temperature (such as 100° C.) to produce a viscous material. Then, 900 g of rosin or turpentine and 180 ml of an aqueous 28% ammonia solution are mixed and the resultant mixture is heated at a suitable temperature (such as 80 to 100° C.) (preferably under reflux) to evaporate the water content thereof substantially completely and consequently produce a jelly-like material. Finally, the viscous material and the jelly-like material are mixed and the resultant mixture is heated at a temperature of about 100° C. to 120° C. to remove substantially all of the water contained therein. Where the formulation (2) is adopted, the burnt alum may be incorporated into the mixture of the viscous material and the jelly-like material. Consequently, there is obtained a solid substance substantially free from water and capable of resisting against nicotine.

For actual use of the anti-nicotine agent which is obtained as described above, the agent may be orally consumed as is in amounts approximately 100 mg each several times a day or drink the agent in an amount about 500 mg one time a day with water. Otherwise, the anti-nicotine agent is added to caramel, chewing gum or troche in an approximate amount of 60 to 120 mg per piece (2 to 3 grams) by an ordinary method, so that the smoker may use the caramel, chewing gum or troche at a rate of one to three pieces each three or four times a day.

EXAMPLE

An acute nicotine-poisoning test was performed on mice for the purpose of evaluating the anti-nicotine property of the agent of this invention. This test was carried out by orally administering various substances to mice in advance and, 30 minutes after the oral administration, a dilute solution of nicotine was injected into each mouse intravenously through the tail in an amount containing an $LD_{100}$ dose of nicotine. Then, a count was taken of the mice which survived the poison and the ratio of survival was calculated. The results of this test were as shown in the following table.

In this test, six groups each of 10 mice individually weighing about 15 g were used. The test specimens used in this test were a viscous material (hereinafter referred to as Specimen A) prepared by mixing 1,350 g of dextrose or maltose and 30 ml of glacial acetic acid and heating the resultant mixture at a suitable temperature; a jelly-like material (hereinafter referred to as Specimen B) prepared by mixing 900 g of rosin or turpentine and 180 ml of an aqueous 28% ammonia solution and heating the resultant mixture at a suitable temperature; burnt alum (hereinafter referred to as Specimen C); a solid substance (hereinafter referred to as Specimen D) prepared by mixing Specimen A and Specimen B and heating the resultant mixture at a suitable temperature and a solid substance (hereinafter referred to as Specimen E) prepared by mixing Specimen A, Specimen B and 60 g of burnt alum and heating the resultant mixture at a suitable temperature. In mice, the minimum lethal dose of nicotine which causes 100% of death (L.D.$_{100}$) is 0.15 ml of an aqueous 0.0005% nicotine solution per 15 g of body weight. In this test, therefore, this lethal dose was used.

| Test No. (group of 10 mice) | Amount of specimen administered per 15 g of body weight of individual mouse | Amount of aqueous nicotine solution administered to individual mouse | Average ratio of survival |
|---|---|---|---|
| 1 | 0.3 ml of an aqueous solution obtained by dissolving 1 g of Specimen A in 20 ml of water | 0.15 ml of aqueous 0.0005% nicotine solution | 70% |
| 2 | 0.3 ml of a suspension obtained by suspending 1 g of Specimen B in 20 ml of water | Same as above | 60% |
| 3 | 0.3 ml of an aqueous solution obtained by dissolving 1 g of Specimen C in 20 ml of water | Same as above | 30% |
| 4 | 0.3 ml of a suspension obtained by suspending 1 g of Specimen D in 20 ml of water | Same as above | 90% |
| 5 | 0.3 ml of a suspension obtained by suspending 1 g of Specimen E in 20 ml of water | Same as above | 100% |
| 6 | None | Same as above | 0% |

Separately, the compositions of the anti-nicotine agent of the present invention were tested by the so-called Magnus Method by way of investigation of possible effects on the autonomic nerves in the intestinal canals taken out of rabbits.

Further, for the purpose of evaluating the effectiveness of the product in detoxiating chronic nicotine poisoning, the following test was performed: The following four groups each of which had ten albino rats (50 to 60 g per head of body weight) at the age of about one month were respectively raised in the same conditions: (1) The control group given no treatment, (2) the group administered nicotine (involving hypodermic injection of a daily dose of 0.02 mg of nicotine per kg of body weight), (3) the group administered the product (involving oral administration of a daily dose of 25 mg of the product per kg of body weight) and (4) the group administered a combination of nicotine and the product (involving administration of a daily dose of 0.02 mg of nicotine and a daily dose of 25 mg of the product respectively per kg of body weight). The results of the test reveal that the group of nicotine administration began to show a sign of retarded growth about ten days after starting the test as compared with the control group and that the degree of retardation of growth increased with the increasing duration of the test. In the meantime, the group administered nicotine and the product in combination showed a smooth growth. The group administered only the product showed a slightly better growth than the control group.

What is claimed is:
1. An anti-nicotine agent prepared by the steps of:
    mixing (a) 45 to 450 parts by weight of a monosaccharide or disaccharide and (b) 1 to 10 parts by weight of acetic acid or glacial acetic acid, and heating the resultant mixture to produce a viscous material;
    mixing (c) 30 to 300 parts by weight of rosin or turpentine and (d) 1.68 to 16.8 parts by weight of ammonia in the form of an aqueous solution, and heating the resultant mixture to produce a jelly-like material; and
    mixing said viscous material and said jelly-like material, and heating the resultant mixture to remove substantially all water.
2. The anti-nicotine agent of claim 1 wherein (a) is dextrose or fructose.
3. The anti-nicotine agent of claim 1, wherein (a) is maltose.
4. The anti-nicotine agent of claim 1, wherein 2 to 20 parts by weight of burnt alum are additionally mixed with said mixture of viscous material and jelly-like material prior to heating.

* * * * *